US006821771B2

(12) United States Patent
Festoc

(10) Patent No.: US 6,821,771 B2
(45) Date of Patent: Nov. 23, 2004

(54) DEVICE FOR THERMO-DEPENDENT CHAIN REACTION AMPLIFICATION OF TARGET NUCLEIC ACID SEQUENCES, MEASURED IN REAL-TIME

(75) Inventor: Gabriel Festoc, Rennes (FR)

(73) Assignee: Genesystems, Bruz (FR)

(*) Notice: Subject to any disclaimer, the term of this patent is extended or adjusted under 35 U.S.C. 154(b) by 262 days.

(21) Appl. No.: 09/981,070

(22) Filed: Oct. 15, 2001

(65) Prior Publication Data

US 2002/0081669 A1 Jun. 27, 2002

Related U.S. Application Data

(63) Continuation of application No. PCT/FR01/02385, filed on Jul. 20, 2001.

(30) Foreign Application Priority Data

Jul. 28, 2000 (FR) ........................................... 00 10029

(51) Int. Cl.$^7$ ........................... C12M 1/34; C12Q 1/68; C12P 19/34; C07H 21/02; C07H 21/04

(52) U.S. Cl. ......................... 435/287.2; 435/6; 435/7.1; 435/91.1; 435/91.2; 536/22.1; 536/23.1; 536/24.3; 536/24.31; 536/24.32; 536/24.33

(58) Field of Search ........................... 435/6, 7.1, 91.1, 435/91.2, 287.2; 530/22.1, 23.1, 24.3–24.33

(56) References Cited

U.S. PATENT DOCUMENTS 5,446,263 A 8/1995 Eigen et al.
6,063,589 A * 5/2000 Kellogg et al. ............... 435/24
6,303,343 B1 * 10/2001 Kopf-Sill ................... 435/91.1

FOREIGN PATENT DOCUMENTS

| | | |
|---|---|---|
| DE | 198 10 499 | 9/1999 |
| DE | 198 52 835 | 5/2000 |
| FR | 2 672 231 | 8/1992 |
| GB | 1 572 596 | 7/1980 |
| WO | WO98/49340 | 11/1998 |
| WO | WO00/33962 | 6/2000 |

OTHER PUBLICATIONS

Heid, C.A., et al., "Real Time Quantitative PCR", Genome Methods, Cold Spring Harbor Laboratory Press, 6:986–994, 1996.

Gibson, U., et al., "A Novel Method for Real Time Quantitative RT–PCR", Genome Methods, Cold Spring Harbor Laboratory Press, 6:995–1001, 1996.

Cohen, H., et al., "PCR Amplification of the fimA Gene Sequence of *Salmonella typhimurium*, —*a Specific Method for Detection of Salmonella spp.*", Applied and Environmental Microbiology, vol. 62, No. 12, p. 4303–1308, Dec., 1996.

Williams, P., et al., "Development and Application of Real-Time Quantitative PCR", p. 313–325, 1998.

* cited by examiner

*Primary Examiner*—Jeffrey Siew
(74) *Attorney, Agent, or Firm*—Merchant & Gould P.C.

(57) ABSTRACT

The present invention concerns a device for amplifying target nucleic acids, reaction cartridge s for use in the device, and modes of use of the device.

18 Claims, 11 Drawing Sheets

DEVICE FOR THERMO-DEPENDENT CHAIN REACTION AMPLIFICATION OF TARGET NUCLEIC ACID SEQUENCES, MEASURED IN REAL-TIME

This application is a continuation of international application No. PCT/FR01/02385, filed Jul. 20, 2001, pending.

FIELD OF THE INVENTION

The present invention concerns the field of genetics.

More precisely, the present invention relates to a device for amplifying target nucleic acid sequences, to reaction cartridges for use in the device, and to methods of application of this device.

The aim of the present invention is the detection and, if required, real-time quantification of target nucleic acid sequences in one or more samples.

BACKGROUND AND PRIOR ART

Detecting target nucleic acid sequences is a technique that is being used to a greater and greater extent in many fields, and the range of applications of that technique is predicted to widen as it becomes more reliable, cheaper and faster. In the human health field, detecting certain nucleic acid sequences can in some cases provide a reliable and rapid diagnosis of viral or bacterial infections. Similarly, detecting certain genetic peculiarities can allow susceptibilities to certain diseases to be identified, or provide an early diagnosis of genetic or neoplastic diseases. The detection of target nucleic acid sequences is also used in the agroalimentary industry, in particular to provide product traceability, to detect the presence of genetically modified organisms and to identify them, or to carry out food checks.

Detection procedures based on nucleic acids almost systematically involve a molecular hybridisation reaction between a target nucleic acid sequence and one or more nucleic acid sequences complementary to that target sequence. Such processes have a number of variations, such as techniques known to the skilled person as “transfer techniques” (blot, dot blot, Souther blot, Restriction Fragment Length Polymorphism, etc.), or such as miniaturised systems on which the complementary sequences of the target sequences are previously fixed (microarrays). Within the context of such techniques, complementary nucleic acid sequences are generally termed probes. A further variation, which can in itself constitute the basis of a diagnostic procedure or may simply be a supplementary step in one of the techniques mentioned above (in particular to increase the concentration of the target sequence and thus, the sensitivity of the diagnosis), consists of amplifying the targeted nucleic acid sequence. A number of techniques that can specifically amplify a nucleic acid sequence have been described, the most popular technique being the Polymerase Chain Reaction (PCR). Within the context of that technique, complementary nucleic acid sequences of target sequences, termed primers, are used to amplify those target sequences.

PCR reactions involve repeated cycles, generally 20 to 50 in number, and each is composed of three successive phases, namely: denaturation, primer annealing, strand elongation. The first phase corresponds to transforming double-stranded nucleic acids into single-stranded nucleic acids; the second phase is molecular hybridisation between the target sequence and the complementary primers for said sequence, and the third phase corresponds to elongation of the complementary primers hybridised to the target sequence, using a DNA polymerase. Those phases are carried out at specific temperatures: generally, 95° C. for denaturation, 72° C. for elongation, and between 30° C. and 65° C. for annealing, depending on the melting temperature (Tm) of the primers used. It is also possible to carry out the annealing and elongation steps at the same temperature (generally 60° C.).

Thus, a PCR reaction consists of a sequence of repetitive thermal cycles during which the number of target DNA molecules acting as the template is theoretically doubled for each cycle. In practice, the PCR yield is less than 100%, so the quantity of product $X_n$ obtained after n cycles is:

$$X_n=X_{n-1}(1+r_n),$$

where $X_{n-1}$ is the quantity of product obtained in the preceding cycle, and $r_n$ is the PCR yield in cycle n ($0<r_n\leqq 1$).

Assuming the yield to be a constant, i.e., identical for each cycle, the quantity of product $X_n$ obtained after n cycles from an initial quantity $X_0$ is:

$$X_n=X_0(1+r)^n \quad \text{(A)}$$

In practice, the yield r reduces during the PCR reaction, due to a number of factors such as a limiting quantity of at least one of the reagents necessary for amplification, deactivation of the polymerase by its repeated passes at 95° C., or its inhibition by pyrophosphates produced by the reaction.

Because of this reduction in yield, the PCR reaction kinetics firstly exhibit an exponential phase (where r is a constant), which then changes into a plateau phase when r reduces.

During the exponential phase, equation (A) above applies, and can also be written as:

$$\log(X_n)=\log(X_g)+n\log(1+r)$$

Thus, in the exponential phase of the PCR, the curve showing the quantity of product on a logarithmic scale as a function of the number of cycles is a straight line with slope (1+r) which intersects the ordinate at a value equal to the logarithm of the initial concentration.

Real-time measurement of the quantity of product obtained can thus provide the initial concentration of the template, which is of particular importance in a large number of applications, for example when measuring the viral change in a patient, or to determine the variability of a transcriptome.

Generally, the PCR employs reaction volumes of 2 $\mu$l to 50 $\mu$l and is carried out in tubes, microtubes, capillaries or systems known in the art as “microplates” (integral assemblies of microtubes). Each batch of tubes or equivalent containers must thus be successively heated to the three temperatures, corresponding to the different phases of the PCR, for the desired number of cycles.

Using tubes or similar systems obliges the operator to carry out many manipulations to prepare as many tubes and solutions (known in the art as mix PCR) as there are target sequences to be amplified, even when using a single sample of nucleic acids, with the exception of multiplex amplification procedures, which amplify a plurality of target sequences simultaneously in the same container, either using low specificity primers that can hybridise with a plurality of target sequences, such as RAPD—random amplified polymorphism DNA, or using specific primers in larger numbers, where each pair of primers used amplifies a single target sequence. Multiplex amplifications correspond to particular cases and are not in routine use. Further, they do not guarantee freedom from interactions of one amplification reaction with another, and because of possible hybridisations between primers, can only be very limited in the number of target sequences amplified per container.

Those different manipulations cause a number of disadvantages.

Firstly, they are time consuming. Secondly, they are not risk-free as regards possible contamination from one tube to another or from the external environment (dust, bacteria, aerosols or other contaminants that may contain nucleic acid molecules or molecules that may influence the efficacy of the amplification reaction). Further, homogeneity of volume and reagent concentration from one tube to another is not guaranteed. Finally, the volumes are necessarily manipulated manually and are generally greater than 1 $\mu$l, which affects the costs of carrying out PCR as the reagents employed are expensive.

The use of devices designed for at least partial automation of such manipulations can overcome some of those disadvantages. However, those instruments are relatively expensive and their use is, therefore, only economically justified when carrying out many PCR amplifications, for example for genome sequencing.

Some instruments also exist that can carry out kinetic PCR amplifications. As seen above, kinetic PCR necessitates real-time, specific quantification of the amplified target sequence. The use of a fluorescent reporter in the reaction mixture allows the increase in the total quantity of double-stranded DNA to be measured in that mixture. However, that method cannot discriminate amplification of the target sequence from background noise or from possible non specific amplification. Several probe systems have recently been described that specifically measure amplification of a set target sequence. They are based on complementary oligonucleotides of that sequence, and bonded to pairs of fluorophore groups or fluorophore/quenchers, such that hybridisation of the probe to its target and the successive amplification cycles cause an increase or reduction in the total fluorescence of the mixture, depending on the case, proportional to the amplification of the target sequence.

Examples of probes that can be used to carry out kinetic PCR that can be cited are the TaqMan™ (ABI®), the AmpilSensor™ (InGen), and the Sunrise™ (OnCor®, Appligène®) systems.

The system in most widespread use is the TaqMan™ system.

That procedure combines activities of DNA polymerase and the 5'→3' nuclease of Taq polymerase during PCR. The principle is as follows: in addition to the two primers with a sequence complementary to that of the target to be amplified, a probe, the reporter probe, is added to the reaction medium. It has the ability to hybridise with the target in the body of the amplified sequence, but cannot itself be amplified. A phosphoryl group added to the 3' end of the probe prevents it from being extended by Taq polymerase. A fluorescein derivative and a rhodamine derivative are incorporated into the probe, respectively at the 5' and 3' ends. The probe is small, so the rhodamine derivative located close to the fluorescein absorbs the energy emitted by the fluorescein when it is excited (quenching).

Once the primers are hybridised to the target, during the elongation reaction. Taq DNA polymerase attacks the probe via its 5' nuclease activity, releasing the quencher group and thus re-establishing fluorescence. The intensity of the emitted fluorescence is then proportional to the quantity of PCR products formed, which provides a quantitative result. The emitted fluorescence is proportional to the initial number of target molecules. The fluorescence development kinetics can be followed in real-time during the amplification reaction.

That technique has the advantage of being capable of ready automation. An instrument that can carry out the technique, the ABI Prism 7700™, is sold by Perkin-Elmer. That instrument combines a thermocycler and a fluorimeter. It can detect the increase in fluorescence generated during a quantification test using the TaqMan™ procedure, by means of optical fibres located under each tube and connected to a CCD camera that detects, in real-time, the signal emitted by the fluorescent groups liberated during PCR. Quantitative data are deduced by determining the cycle at which the signal from the amplification product reaches a certain threshold determined by the operator. Several studies have demonstrated that the number of cycles is proportional to the quantity of initial material (Gibson, Heid et al., 1996; Heid, Stevens et al., 1996; Williams, Giles et al., 1998).

The number of potential applications of such an instrument is considerable, in human health, in the agroalimentary field and in quality control. Unfortunately, the ABI Prism 7700™ and the several other competing instruments currently on the market are extremely expensive. Further, they can only be used by a trained operator. In practice, such instruments are only used in certain highly specialised areas.

Thus, there is a need for a nucleic acid amplification system, if necessary measuring in real-time, which does not have the disadvantages of the prior art mentioned above.

SUMMARY OF THE INVENTION

The present invention aims to provide such a system that can considerably reduce the number of manipulations required to carry out an amplification method on a plurality of target sequences and as a result, to reduce the time necessary for this operation.

The present invention also provides such a system that minimises the risk of contamination between containers.

The present invention further provides such a system that reduces the volumes of reagents used, thereby reducing the costs involved.

Still further, the present invention provides such a system that optimises homogeneous volume distribution and concentration of the reagents required for PCR in the containers.

Yet still further, the invention provides, for all potential users, in particular for hospitals, medical analytical laboratories, agroalimentary industrialists and health control laboratories, a device that is easy to use and maintain, to routinely carry out real-time quantitative nucleic acid amplifications.

Some of the terms used in the present application have the following meanings:

A "nucleic acid amplification reaction" refers to any method for amplifying nucleic acids that is known in the art. Non-limiting examples that may be cited are PCR (polymerase chain reaction), TMA (transcription mediated amplification), NASBA (nucleic acid sequence based amplification), 3SR (self sustained sequence replication), SDA (strand displacement amplification) and LCR (ligase chain reaction). The initial amplification template can be any type of nucleic acid, DNA or RNA, genomic, plasmid, recombinant, cDNA, mRNA, ribosomal RNA, viral DNA or the like. When the initial template is an RNA, an initial reverse transcription step is generally carried out to produce a DNA template. This step will not generally be mentioned in the text, as the skilled person will know exactly when and how to carry it out. Clearly, the devices of the invention can be used to amplify and possibly specifically quantify RNA sequences as well as DNA sequences. In the remainder of the text, the term "PCR" will thus be the generic term used to designate both PCR proper and RT-PCR (reverse transcription-polymerase chain reaction).

Some of the amplification reactions cited above are isothermal. Others, in particular PCR and LCR, necessitate heating the reaction mixture to different temperatures at different times in a cyclic manner. Such reactions are termed "thermodependent nucleic acid amplification reactions". In the remainder of the text, the device of the invention will be principally described with respect to its application to PCR. However, it is clear that this device is not limited to this technique and it can also be used for any nucleic acid amplification reaction or even for other enzymatic and/or molecular biological reactions. This device is particularly suitable for reactions that require small volumes where the reaction mixture is cycled at a plurality of temperatures, as will become clear from the following description.

One of the aims of the present invention is to provide a novel instrument for carrying out quantitative amplification reactions, i.e., reactions that enable the concentration of the target sequence initially present in the reaction mixture to be determined. Several types of quantitative amplification reactions have been described. A distinction can be made between quantitative amplifications based on the use of an external standard, competitive amplifications, using an internal standard, and kinetic amplifications, the principle of which has been described above, which consist of real-time measurement of the increase in the quantity of target sequence. This type of amplification will be termed "kinetic amplification (of nucleic acids)", "kinetic PCR", "real-time quantitative amplification (of nucleic acids)" or "real-time PCR". The terms in brackets are occasionally omitted.

In this application, the term "reagent" should be construed in its broad sense, as meaning any element necessary either for the amplification reaction proper or for its detection. In accordance with this definition, the salts, dNTPs, primers and polymerase are reagents required for PCR. Similarly, a fluorescent reporter or a probe are also considered here to be reagents participating in detection of the amplified products, although they do not react in the literal sense.

Other terms designating certain elements of the instrument of the invention will be described below in the detailed description of the invention.

Certain elements of the instrument are shown in the drawings, which illustrate several non-limiting embodiments and variations of the invention, and in which:

BRIEF DESCRIPTION OF THE DRAWINGS

FIG. 11 shows a rectangular cartridge and two models of use for that cartridge.

DETAILED DESCRIPTION OF THE PREFERRED EMBODIMENTS

Figure 1:
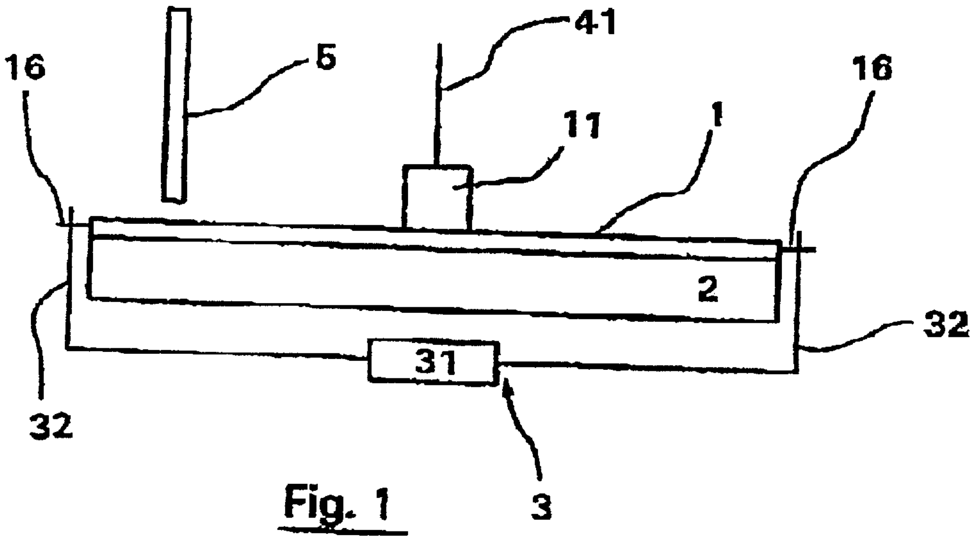
FIG. 1 shows a side view of a simplified embodiment of the instrument of the present invention.

In a first aspect, the invention concerns a device for carrying out enzymatic and/or molecular biological reactions requiring at least two different incubation temperatures, characterized that it comprises:

at least one plate or cartridge (1) having a plurality of reaction chambers (13) and a reservoir (11), said reaction chambers being connected to the reservoir via channels (12);

at least one heating plate (2) having at least two distinct zones that can be heated to at least two different temperatures;

means (3) for relative displacement between said cartridge and said plate, allowing a cyclic variation in the temperature of the reaction chambers.

The temperature in each zone of the plate can be homogeneous or, if necessary, the temperature can vary along a gradient.

Several types of molecular biological reactions require the reaction mixture to be subjected to different temperatures at various times. This is the case, for example, when an enzyme has to be deactivated after use (for example, a restriction nuclease), or to test the stability of a complex. In the latter case, a complex (for example, an antigen/antibody complex, or a receptor/ligand complex) where one of the elements is coupled to a fluorophore and the other to a fluorescence quencher, may be placed in one of the reaction chambers of the instrument. The plate is then programmed to produce several temperatures in increasing order, if necessary in the form of a gradient. The stability of the complex is then tested by displacing the cartridge on the plate, such that the temperature of the reaction chamber increases progressively, and observing the increase in fluorescence using fluorescence excitation/measurement means facing the reaction chamber. An increase in fluorescence equates to dissociation of the complex.

The device of the invention is particularly suitable for reactions requiring a cyclic variation in the temperature of the reaction chambers, which is the case for certain nucleic acid amplification reactions, for example for the polymerase chain reaction (PCR) or for the ligase chain reaction (LCR).

In particular, the invention concerns a device for thermodependent chain reaction amplification of target nucleic acid sequences, characterized in that it comprises:

at least one cartridge (1) having a plurality of reaction chambers (13) and a reservoir (11), said reaction chambers being connected to the reservoir via channels (12);

at least one heating plate (2) having at least two distinct zones that can be heated to at least two different temperatures, corresponding to the amplification cycles for said target nucleic acids;

means (3) for relatively displacement between said cartridge and said plate, allowing a cyclic variation of the temperature of the reaction chambers.

Such a system of the invention is less complex than prior art systems, in that the temperatures necessary for the chain reaction amplification cycles are provided by distinct constant temperature zones, and not by a block the temperature of which is varied.

It is important to note that thermodependent chain amplification reactions require that the samples are subjected to at least two temperatures. As an example, each PCR cycle requires a phase at about 95° C. to denature the target DNA, then a phase between 55° C. and 65° C. (depending on the Tm of the probes), to produce hybridisation/ligation. Regarding PCR, each cycle generally consists of three phases, namely denaturation at about 95° C., annealing the temperature of which depends on the primers Tm, and elongation, normally carried out at 72° C. However, PCR can be carried out with simplified cycles, in which annealing and elongation are carried out at the same temperature, such that each cycle requires only two different temperatures.

Different variations in the device described above can be envisaged. In a preferred variation of the invention, the system comprises the following features:

primers specific for the target sequences to be amplified are pre-distributed in the reaction chambers (13);

the reservoir (11) is intended to receive a fluid composed of a sample of nucleic acids to be analysed and the reagents required for a polymerase chain amplification reaction, with the exception of primers;

the heating plate (2) has three distinct zones that can be heated to three different temperatures corresponding to the three phases of polymerase chain reaction amplification cycles.

In a preferred variation, it is possible to distribute, from a reservoir, a fluid containing a sample of nucleic acids to be analysed and the reagents necessary for PCR in a plurality of reaction chambers containing specific primers for the target nucleic acid sequences to be amplified, and to cause the amplification process by continuously subjecting the contents of the chambers to different temperatures in succession (namely those required for denaturation, annealing and elongation) a plurality of times by means of a relative movement between the cartridge including said reaction chambers and said heating plate having two or three distinct zones that can be heated to different temperatures.

If necessary, the reaction chambers (13) can contain the reagents necessary for a real-time PCR reaction other than the primers mentioned above. In a preferred embodiment of the instrument of the invention, the reaction chambers also comprise, in addition to the primers, one or more probe(s) that are specific to the sequence to be amplified. The distribution of the probes in the reaction chambers can also be such that certain chambers comprise probes specific to the sequences to be amplified and other chambers comprise control probes, which do not a priori recognise the sequence to be amplified. These probes can be labelled and, if a plurality of probes are present in one and the same reaction chamber (for example a probe specific to the sequence to be amplified and a control probe), these probes will preferably be labelled with different fluorophores.

In a further variation of the instrument, supplementary reagents, such as dNTPs or salts, are initially deposited in the reaction chambers. These reagents will then be absent or present in lower qualities in the fluid deposited in the reservoir (11). In the extreme case, all of the reagents necessary for the PCR reaction, with the exception of the template, are deposited in the reaction chambers (13), and the fluid deposited in the reservoir (11) will then comprise solely the DNA (or RNA) sample to be amplified.

The variations described above assume that a plurality of reactions are carried out in parallel, with different primers and/or probes, on the same sample. It then concerns the characterisation of a unique sample (or several samples if the reservoir is divided into several sub-reservoirs) in accordance with several criteria. In contrast, some applications require the characterisation of a multitude of samples in accordance with a single criterion or a small number of criteria. This is the case, for example, in research, when a library of phages or bacteria is to be screened for the presence of a given gene. In this case, PCR has to be carried out on a large number of samples from a given pair of primers. The device of the invention is also adapted to this type of manipulation. To this end, the samples are deposited in the reaction chambers (13). The primers can be introduced into the fluid deposited in the reservoir (11), with the other reagents required for PCR. Clearly, this configuration does not exclude the fact that certain reagents other than the sample to be analysed can be pre-deposited in the reaction chambers (13).

Regardless of the selected variation of the instrument, and regardless of the reagents deposited in the reaction chambers (13), they can advantageously be deposited simply by depositing a liquid, followed by drying. The arrival of fluid from reservoir (11) can then dissolve these reagents. The quantity of each deposited reagent is calculated as a function of the volume of fluid that will penetrate into each reaction chamber (13), such that dissolving the reagents produces the final desired concentration for each chamber. Cartridges such as those described above, in which at least a portion of the reaction chambers (13) comprise reagents that are loaded thereinto by depositing a liquid followed by drying, such that these reagents are dissolved by the arrival of fluid in the reaction chambers, also form an integral part of the invention.

The instrument described above has the advantage of simultaneously filling all the reaction chambers, which reduces the preparation time and the risks of contamination from one chamber to another. This instrument also has the advantage of being capable of miniaturisation and means that smaller volumes of reagents can be used than was customary with the prior art.

Finally, it can also be noted that, because of the specific heating plate that is recommended, the invention can accelerate the PCR cycles since the different phases (denaturation, annealing, elongation) are not carried out by varying the temperature of the heating plate or the atmosphere as in the prior art, the relative movement between the cartridge and the plate enabling the contents of each of the reaction chambers to be rapidly and successively subjected to the three distinct temperatures of these phases. The use of low reaction volumes, and of a thin floor for the cartridge (1), can also limit thermal inertia in the reaction chambers, and thus contributes to the rapidity of the reaction.

The invention also concerns a device for thermodependent amplification of target nucleic acid sequences, measured in real-time, characterized in that it comprises the same elements as in any one of the devices described above, and also comprises optical fluorescence excitation/measurement means (5), disposed so as to excite and measure the fluorescence of the contents of the reaction chambers for each cycle.

One of the particularly original elements of the devices described above is the element termed either the plate or reaction cartridge (1). This element can be recyclable or, as is preferable, disposable, and as such constitutes a further aspect of the present invention. The invention also provides a reaction cartridge comprising a plurality of reaction chambers (13) and at least one reservoir (11) and has the following characteristics:

each reaction chamber is connected to the reservoir via a channel (12) having a cross section included in a circle with a diameter of least than 3 mm;

the capacity of the reservoir is less than 10 ml;

the disposition of the reaction chambers and the channels with respect to the reservoir allows a fluid to be homogeneously distributed into the reaction chambers, from the reservoir.

The diameter of the channels is preferably selected so as to be sufficiently small not to allow distribution of the fluid present in the reservoir to the reaction chambers under gravity and to prevent non reproducible filling of the chambers. This diameter is preferably about 0.2 mm or less. Regarding this diameter, it should be noted that the cross section of the channels is preferably circular, but it may be any other shape, in particular polygonal, and the "diameter" of the channels will designate the largest cross sectional dimension.

A variety of capacities can be employed for the reservoir intended to receive the nucleic acid sample and the reagents necessary for PCR, for example in the range of about 0.1 ml to about 1 ml.

The cartridge preferably comprises about 20 to about 500 reaction chambers, more preferably between 60 and 100 reaction chambers.

The volume of these chambers depends on the embodiments. Advantageously, the volume of these chambers is in the range of about 0.2 $\mu$l to 50 $\mu$l, preferably in the range of 1 $\mu$l to 10 $\mu$l.

In the cartridges of the invention, the junction between the channels (12) and the reservoir (11) is preferably produced at the periphery of the reservoir, and the base of said reservoir is inclined and/or convex, so as to ensure distribution of a fluid contained in the reservoir to the inlet to the channels.

It should be noted that a cartridge of the invention can have a multitude of shapes. However, in a preferred variation of the invention, this cartridge is circular in shape, the reservoir then being substantially at the centre of the cartridge, the reduction chambers being distributed in a circle around the reservoir, and the channels connecting the reservoir to the chambers being essentially radial. Such an architecture can optimise filling the reaction chambers from the central reservoir.

In a particular embodiment with a circular cartridge, the base of reservoir (11) is conical.

Preferably again, said reaction chambers are provided at the relative periphery of said chamber. It is possible to optimise the number of reaction chambers that can be provided in the cartridge and filled from the central reservoir.

In a variation of the invention, such a cartridge comprises as many channels as there are reaction chambers. However, in some embodiments, sections of the channels may be common to more than one reaction chamber.

One advantage of the present invention is that the device can readily be miniaturised. Thus, advantageously, when the cartridge has a geometry of revolution, it preferably has a diameter in the range of about 1 to 10 cm.

Figure 11A:
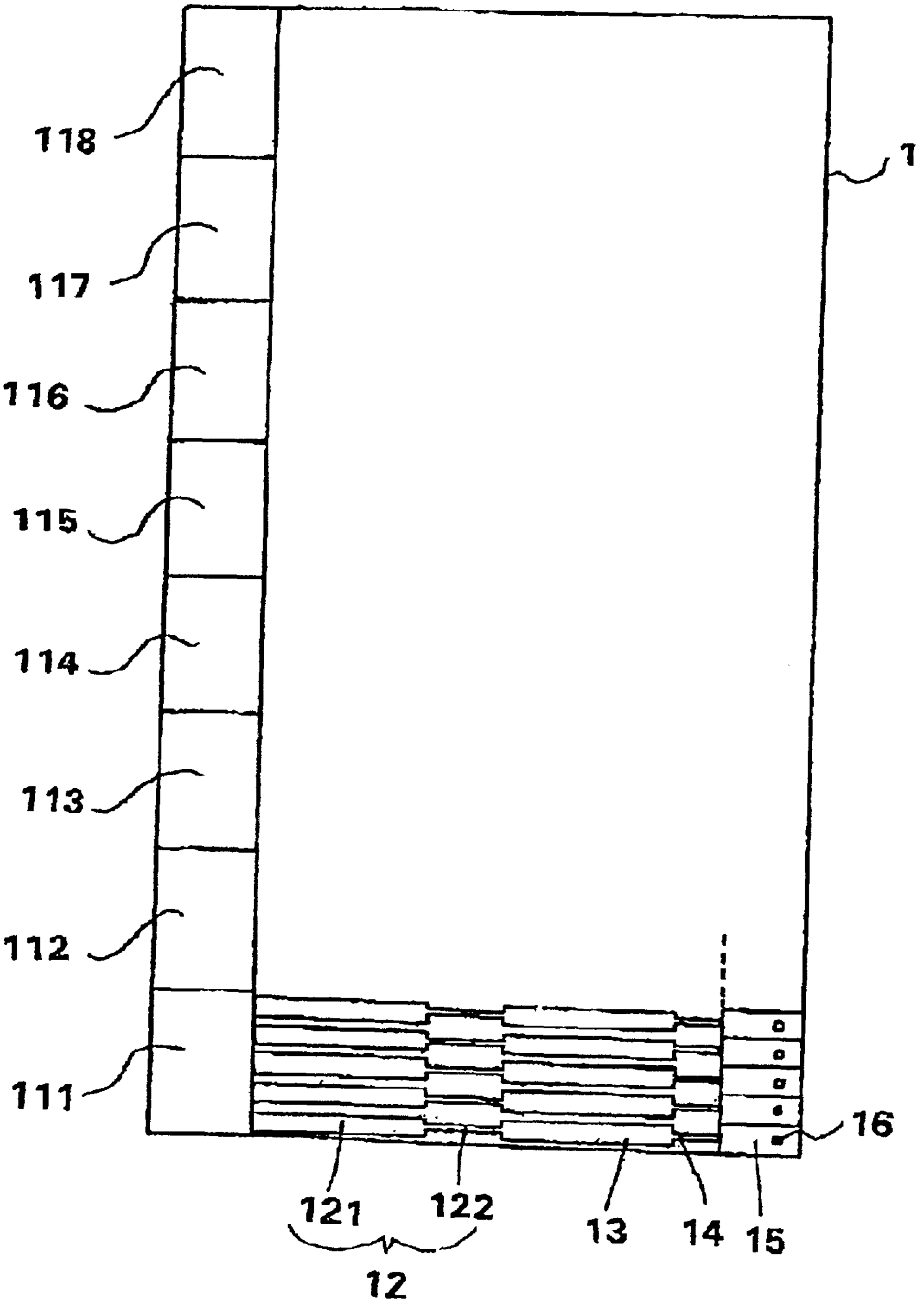
FIG. 11A shows a cartridge (1) comprising eight sub-reservoirs (111 to 118) and 40 reaction chambers. Only the five channels connected to sub-reservoir 111 are shown, along with the corresponding reaction chambers (13).

Alternatively, a cartridge of the invention may possess a translational geometry, in which the reservoir (11) is positioned on one side of said cartridge, the reaction cartridges (13) are aligned on the other side of the cartridge, and the channels (12) connecting the reservoir to the chambers are essentially parallel to each other. The general shape of such cartridge is then essentially rectangular, apart from some protuberances and/or hollows intended to connect the cartridge to means that can cause it to move. An example of such a cartridge is shown in FIG. 11A. In the case of such a cartridge, the bottom of the reservoir (11) is preferably an inclined plane, which directs the reaction fluid towards the inlet to channels (12).

In a variation of the cartridges of the invention described above, regardless of their geometry, reservoir (11) is divided into 2 to 20, preferably 2 to 6, sub-reservoirs, to simultaneously analyse several samples on the same cartridge. In this case, each of the reaction chambers (13) is connected to just one of these sub-reservoirs via a channel (12). An example of this variation is shown in FIG. 11A. The cartridge shown in this figure comprises eight sub-reservoirs numbered 111 to 118, each of the sub-reservoirs being connected to five reaction chambers (13) via five channels (12). In this figure, only the channels connected to the sub-reservoir 111 are shown. It is important to note here that throughout this text, the term "reservoir (11)" designates both the reservoir (11) as a whole, and a sub-reservoir.

The depth of the reaction chambers (compared with the channels) can also vary as a function of the embodiments of the invention. In a preferred variation, the depth of these chambers is in the range of about 0.5 mm to 1.6 mm.

It should also be noted that the thickness of the cartridge depends on several factors, in particular on its constituent material. In practice, this cartridge is preferably constituted by a plastic, preferably a polycarbonate, which has physical, optical and thermal properties that are suited to the present invention. The thickness of the cartridges of the invention is preferably in the range of 0.5 to 5 mm.

In order to facilitate thermal exchanges between the contents of the reaction chambers and the plate, the "floor" thereof is preferably as thin as possible. Its thickness depends on the material used to produce the cartridge. Preferably, it is in the range of 0.05 to 0.5 mm, for example about 0.25 mm.

The reaction chambers for the cartridges of the invention are preferably closed by a transparent upper wall (17), for example of transparent plastic, to allow excitation and measurement of the fluorescence of the reaction fluid, under GMP conditions.

In a particular embodiment of the invention, the chambers are provided with vents (open system) allowing the air they contain to escape when they are filled with the fluid from the reservoir.

In the above case, where the chambers (13) are provided with vents (14), channels (12) are preferably constituted by at least two portions with different diameters (121 and 122), the diameter of the second portion (122) being less than that of the first portion (121), to create a pressure drop in the channel (12). If a channel is filled faster than another channel under the effect of pressure, the pressure drop effect will stop the progress of fluid in the channel or channels where the first portion (121) is filled, until all of the channels have been filled in the same manner. This allows the volumes for each channel to be "pre-calibrated" to ensure homogeneous filling of the different reaction chambers. The second portion of the channel (122) can, for example, be constituted by a glass capillary with a much smaller diameter than that of the first portion (121), said capillary being included in a plastic cartridge.

It is also possible to provide cells (15) into which reaction chamber vents (14) open. These cells have an opening (16) to the cartridge exterior (open system) and have the advantage firstly, of pollution-free recovery of any surplus fluid that could leave the reaction chambers via the vents (14) and secondly, they can be closed after filling the reaction chambers. They can, for example, be closed using adhesive tape, to produce a closed system to carry out the amplification proper. This can avoid or at least limit evaporation of the fluid contained in the cartridge (1). This embodiment is described in Example 3 and illustrated in FIGS. 11A and 12.

Alternatively, a closed system protocol can be used from the point that the reaction chambers are filled, causing an underpressure in the cartridge followed by re-establishing the pressure, as will be described below. Cartridges in which the reaction chambers have no openings other than the channel inlet (12) ("closed" reaction chambers) are also encompassed by the scope of the invention.

The cartridges described above, provided either for use in an open system, or for use in a closed system, preferably comprises an opening adaptable for means (4) for adjusting the pressure in the reservoir (11), to displace the fluid present in the reservoir towards the reaction chambers.

The invention also concerns a method for filling reaction chambers (13) of a cartridge (1) as described in the preceding paragraph in a closed system, wherein the reaction chambers of the cartridge are closed, said method comprising the following steps:

at least partially filling the reservoir (11) with a fluid;

connecting the cartridge (1) to means (4) for adjusting pressure;

applying an underpressure inside the cartridge, then re-establishing the pressure.

In a variation of the cartridges of the invention, each channel (12) is provided with an anti-reflux cavity (123) at its junction with the reservoir (11), said anti-reflux cavity being constituted by a substantially vertical channel portion with a diameter that is greater than or equal to that of channel (12). This variation has two main advantages. Firstly, these anti-reflux cavities can prevent cross-contamination in the case of accidental return to the fluid to the reservoir (11), or in the case where not all of the fluid is engaged in the channels. Further, these enable the instruments of the invention to be provided with a cap the indentations of which fit these vertical inlets, to cap the channels after distribution of the reaction fluid but prior to the amplification reaction. This enables the system to be operated as a completely closed system, and thus avoids any risk of contamination and evaporation. However, it is important to note that the anti-reflux cavities, and the use of a cap in the reservoir to block the inlet to the channels on the reservoir side can also be used in the case of open systems such as those described above, where the reaction chambers are provided with vents.

In a preferred embodiment of the cartridges of the invention, at least a portion of the reaction chambers (13) comprises oligonucleotides. More preferably still, each of the reaction chambers (13) comprises two primers specific for a nucleic acid sequence to be amplified and, optionally, one or more labelled probe(s) specific for said sequence. Such a probe can be labelled such that its signal increases when it hybridises with its target sequence (Sunrise™ system), or so that extension from a strand to which it is hybridised causes a reduction or an increase in the signal (AmpliSensor™ or TaqMan™ system, respectively). The presence of such probes in the reaction chambers enables quantitative real-time amplifications to be carried out with the instrument of the invention provided with fluorescence excitation/measuring means, as described above. Control probes, which are not specific to the sequence to be amplified, and labelled in a different manner to that of the specific probes, can also be used, to detect any contamination.

In the embodiment of the invention described above, where the reaction chambers comprise primers and one or more optional probe(s), these different probes and primers are preferably selected so that their respective melting points (Tm) are close. In particular, the Tm of different primers is preferably within a range about 5° C. Similarly, the different probes will preferably have a Tm within a range of about 5° C., which can be different from the primer range. In this case, the probes will be selected such that their Tm is higher than that of the primers, the difference between the Tm of the different categories of oligonucleotides then preferably being of the order of 5° C. The hybridisation temperature used to carry out amplification then corresponds to the lowest primer melting point.

In addition to primers and optional probes, the reaction chambers (13) of the cartridges of the invention can also comprise one or more other reagents required for the PCR reaction or for measuring amplification. Examples are salts, dNTPs, or a fluorescent double-stranded DNA reporter of the SybrGreen type (registered trade mark). As mentioned above, all of these reagents are advantageously deposited in the reaction chambers (13) by depositing a liquid followed by drying.

In an alternative embodiment of the cartridge of the invention, the cartridges are intended for screening a large number of samples in accordance with a small number of criteria. This implies that the user of the cartridges can readily deposit his samples in each of the reaction chambers (13). To this end, the cartridge can, for example, have a removable cover that gives direct access to the reaction chambers when lifted. Such cartridges can also be precharged and include one or more of the reagents required for amplification and/or detection in the reaction chambers.

Clearly, the devices of the invention mentioned above can comprise one or more cartridges corresponding to any of the cartridges described above.

Figure 2A:
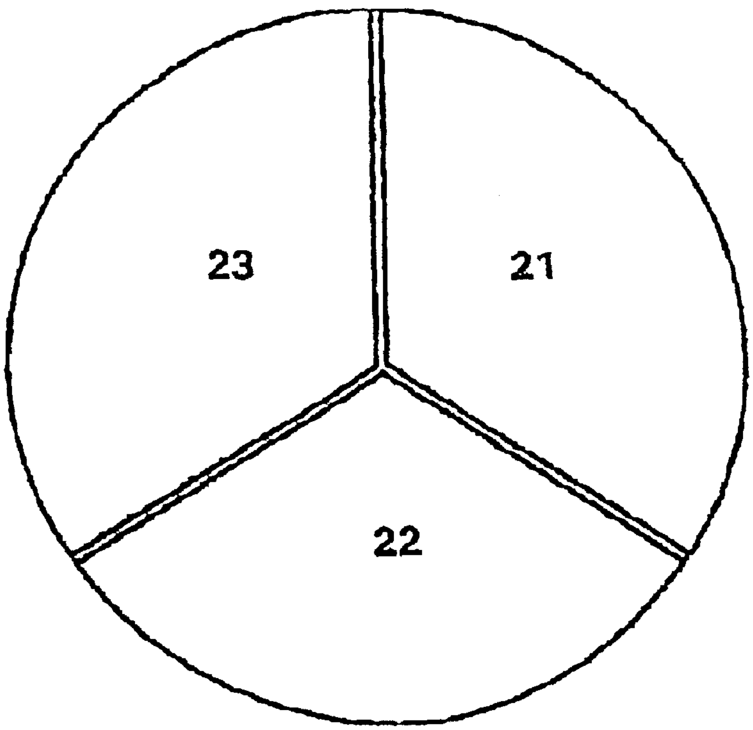
FIG. 2 shows a top view of the heating plate, in the case when the blocks (21 to 23) are sectors of a disk (FIG. 2A) and in the case where they are constituted by sectors of a ring (FIG. 2B)
Figure 2B:
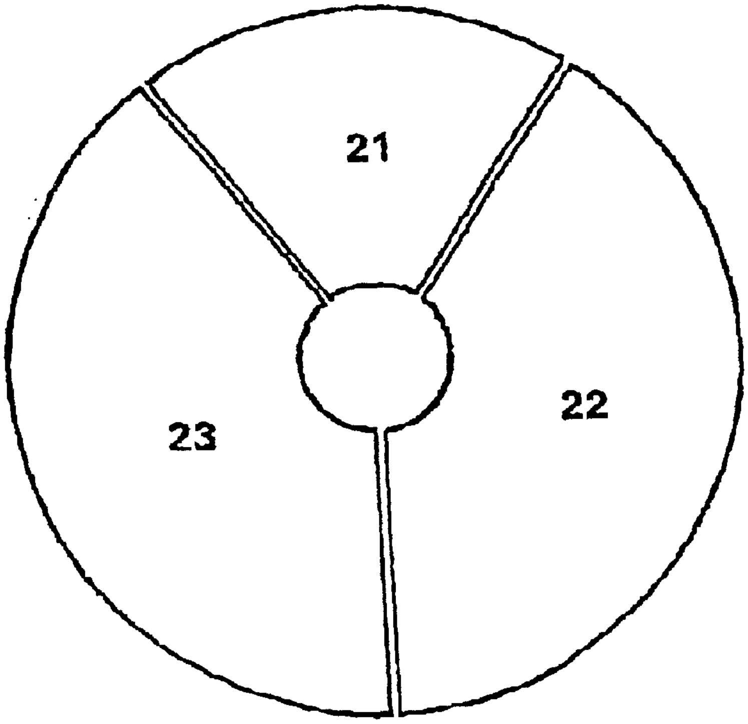
Figure 11B:
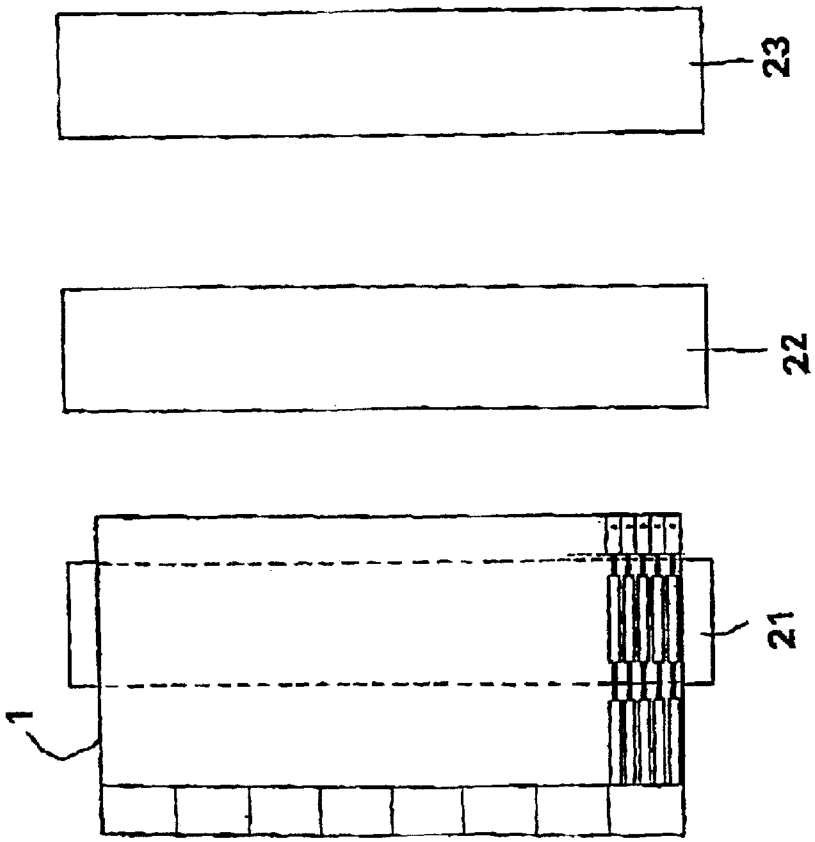
FIG. 11B shows a machine of the invention comprising a rectangular cartridge (1) and a heating plate (2) constituted by three parallel elements (21 to 23).
Figure 11C:
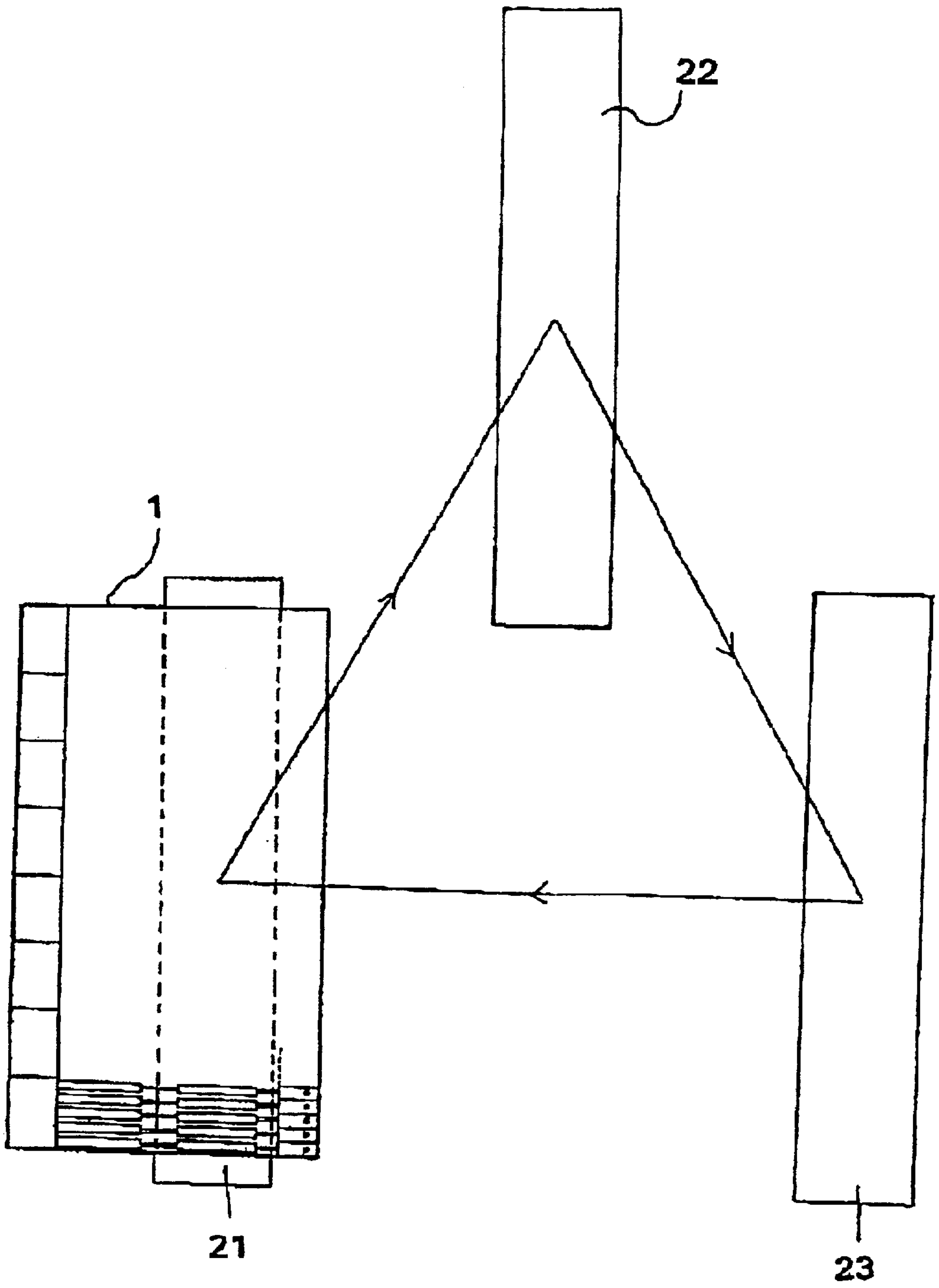
In FIG. 11C, element (22) is offset with respect to the others; the cartridge must then be moved in a triangular path to carry out the PCR cycles.

In the particular embodiment of the device of the invention where the cartridge is circular, distinct heating zones in the heating plate (2) are preferably sections of a disk (FIG. 2A) or a ring (FIG. 2B). Each portion can be heated to a distinct temperature to successively heat the contents of the reaction chambers to the desired distinct temperatures, by hint of means (3) for relative displacement between the cartridge (1) and the heating plate (2). In order to limit problems with evaporation and condensation in the cartridge (1), the thermoblocks are preferably sufficiently wide to heat a portion of the channels as well, as shown in FIG. 11, for example, within the context of a rectangular cartridge.

It is important to note that the number of distinct heating zones can be equal to two, three or more. As an example, in the case of two-temperature PCR, the plate can have a 95° C. zone to denature double-stranded nucleic acids, and a 60° C. zone for primer annealing and elongation. In the case of three-temperature PCR, the plate will have a 95° C. zone (denaturation), a zone between 40° C. and 70° C. (primer annealing) and a zone at 72° C. (elongation). Finally, the plate can have more than three zones, for example to temporarily block the reaction at a given moment in each cycle. The number of zones on the plate can also be a multiple of two or three zones, so that one turn of the cartridge corresponds to several PCR cycles. Finally, it is important to note that the relative size of the different heating zones is advantageously selected so as to be proportional to the incubation period desired for the reaction fluid at the temperature of said zone. In the plate shown in FIG. 2B, the surface area of thermoblock 21, dedicated to the denaturing step, is half that of the thermoblocks intended for the hybridisation and elongation steps (blocks 22 and 23 respectively). By selecting a rotation rate relative to the cartridge on the plate such that one rotation of 360° is carried out in 150 seconds, cycles are obtained in which denaturation takes 30 seconds, hybridisation takes 1 minute and elongation takes 1 minute.

Regarding the displacement means, it should be noted that in a preferred embodiment of the invention, plate (2) is fixed and cartridge (1) is moved by the displacement means (3).

However, in other embodiments, the cartridge may be fixed and the heating plate may be moved by the displacement means.

In a particularly preferred embodiment of the invention, in which the cartridge is circular, the displacement means (3) rotate said cartridge and/or said plate.

A conductive element may be provided between the cartridge and the heating plate. However, in a preferred variation of the invention, said cartridge is in direct contact with said heating plate. In this case, said plate is advantageously provided with a coating encouraging displacement between said cartridge and said plate. Such a coating can, for example, be constituted by Teflon (registered trade mark).

As indicated above, the heating plate of the system can have at least two or three zones that can be heated to distinct temperatures. Preferably, this plate is constituted by two or three distinct independent thermal blocks (thermoblocks) connected to means for programming their temperature. In the case where the plate comprises three thermoblocks (21 to 23), the first of these thermoblocks (21) is heated to the denaturing temperature, the second (22) to the hybridisation temperature, and the third (23) to the elongation temperature. The use of such constant temperature thermoblocks simplifies production of the heating plate.

Figure 10:
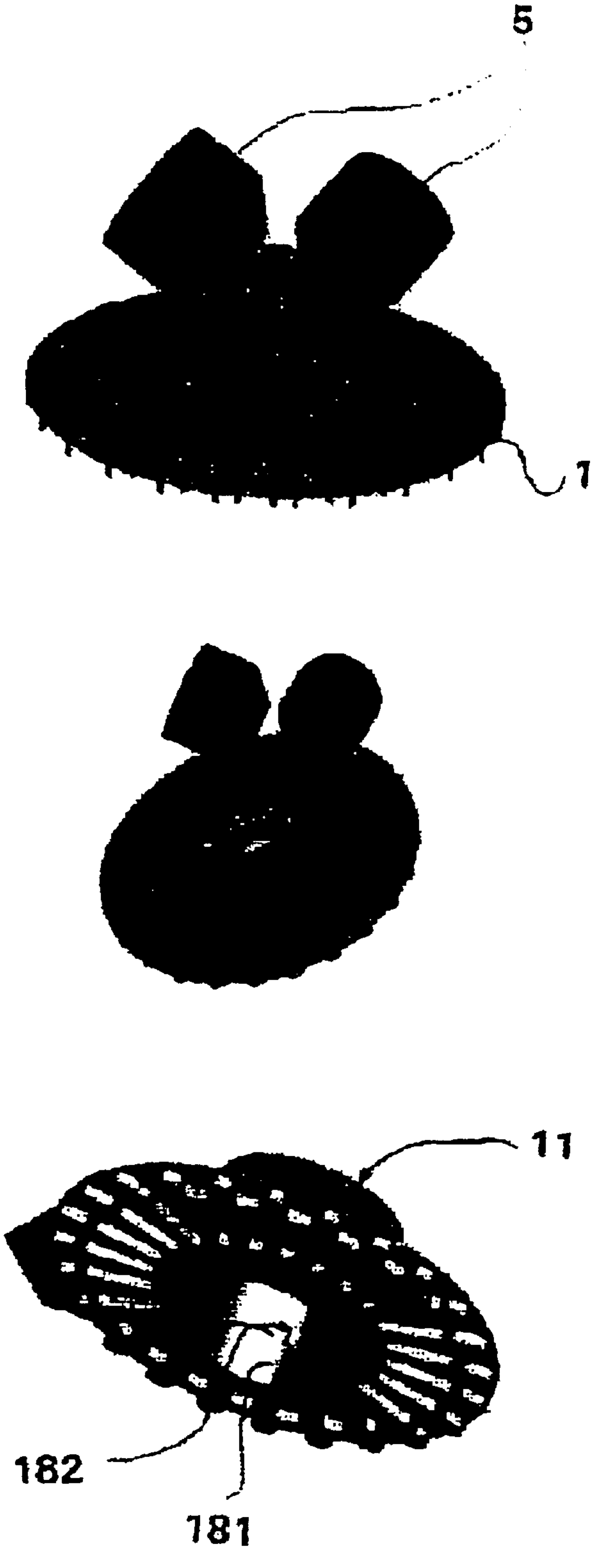
FIG. 10 shows three embodiments of the cartridge of FIG. 9, above which are fluorescence excitation/measurement means (5)

The means for relative displacement of the cartridge with respect to the plate can be produced in many forms, in one preferred embodiment, shown in FIG. 10, the bottom of cartridge (1) has a central projecting portion (181) comprising a notch (182) so that the projecting portion (181) nests in the heating plate (2) and connects the cartridge (1) to the displacement means (3) at a driver or axle (32) that is moved by means of a micromotor (31). The projecting portion (181) acts to position the cartridge with respect to a plate (2) such as that shown in FIG. 2B, and ensures its connection with the moving means (3).

Figure 3:
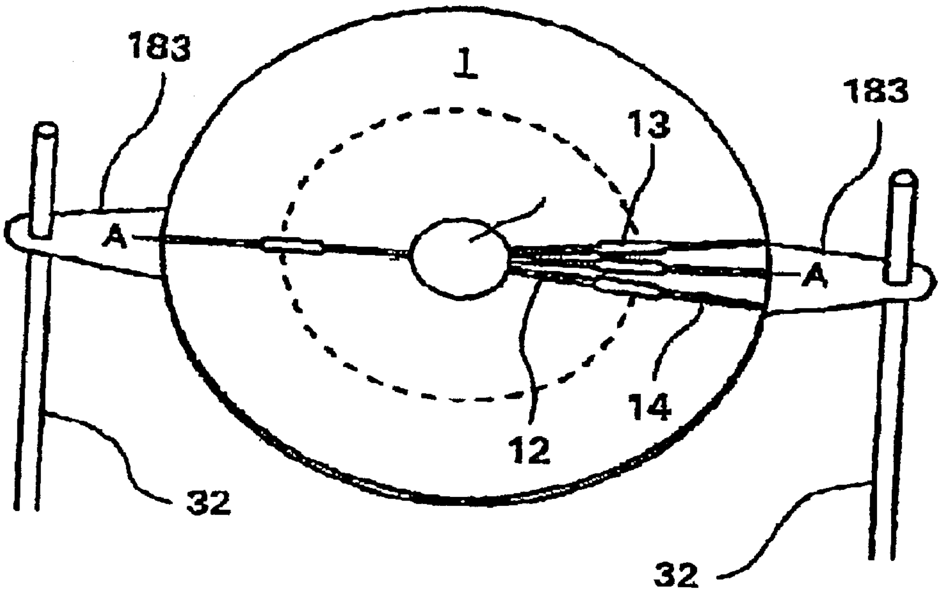
FIG. 3 shows a perspective view of a first embodiment of a cartridge (1) provided with reaction chambers and part of the displacement means.

In an alternative embodiment, shown in FIGS. 1 and 3, the cartridge has at least one lug (183) and the displacement means (3) include at least one axle (32) co-operating with said lug to move said cartridge in a rotary motion.

The mode of relative displacement between the plate and the cartridge can vary depending on the embodiment. It may involve displacement at a continuous rate or intermittently. The displacement rate may be constant, or it may change with time.

In the case of a rectangular cartridge, the cartridge is preferably displaced with respect to the plate (2) by translation, as described in Example 3 and shown in FIG. 11.

Advantageously, the system of the invention also comprises optical fluorescence excitation/measuring means provided, for example, above or to the side of said cartridge. In a preferred variation of the invention, these means will constitute a single fixed system. One advantage of a preferred variation of the invention in which the cartridge is circular and moves in rotation is that it can bring each reaction chamber to a position beneath the optical system in succession, thus reducing its complexity. A registering system, located on cartridge (1), for example, can determine which reaction chamber is located opposite the optical system.

Means for supplying the fluid present in said reservoir to said reaction chambers can be produced in different forms. As has been described above, it is possible to distinguish between two categories of modes of distributing the fluid to the reaction chambers: open system distribution, which assumes an increase in pressure in the reservoir and the presence of vents (14) in the reaction chambers, and closed system distribution, which starts by establishing an underpressure in cartridge (1) followed by re-establishing that pressure.

Means (4) for supplying fluid to the reaction chambers differ depending on the embodiment selected. In the open system, the fluid contained in the reservoir is distributed to the reaction chambers under pressure to allow the chambers to fill in a uniform manner. In this case, the supply means (4) preferably include a piston device (41) with a rate of penetration into the reservoir that is calculated to encourage correct filling of the reaction chambers. Alternatively, these supply means include a pump connected so as to increase the pressure in the reservoir (11).

As seen above, a further preferred variation of the invention involves operating in a closed system. The fluid contained in the reservoir is then distributed to the reaction chambers as follows: firstly, an underpressure is formed inside the cartridge, if necessary using a piston device or a pump (42), this time connected so as to reduce the pressure in cartridge (1). The pressure is then re-established to allow the fluid to engage in the channels and to fill the peripheral reaction chambers.

The invention also concerns any process for nucleic acid amplification using a system as described above, characterized in that it comprises the following steps:

at least partially filling a reservoir (11) with a fluid containing a sample of nucleic acids to be analysed and all that is required for an amplification reaction, with the exception of primers, and optionally, a fluorescent intercalating agent;

distributing said fluid in the reaction chambers (13) provided in the cartridge (1), in which the primers and optionally one or more labelled probes specific for the target nucleic acid sequence is/are distributed;

employing means for relative displacement between the cartridge and the heating plate to successively bring the contents of each chamber to the temperatures defined by the two, three or more zones of said heating plate, as many times as is desired.

In a variation of the above process, the reagents required for the amplification reaction and/or to detect the amplification products, distinct from the primers and probes, are pre-distributed in the reaction chambers (13) of cartridge (1). The fluid introduced into the reservoir (11) then does not contain those reagents.

The step for distributing fluid in reaction chambers (13) is carried out either by applying an underpressure to the interior of the cartridge, then re-establishing the pressure (closed system), or by increasing the pressure in the reservoir (11), provided that the reaction chambers are provided with vents (open system).

The invention and its various advantages will be better understood from the following description of some non limiting embodiments, illustrated in the Figures.

EXAMPLES

Example 1

Simplified Embodiment of the Instrument of the Invention

The system for detecting and quantifying target nucleic acid sequences shown in FIG. 1 comprises a circular cartridge of plastic material 2 mm thick with a diameter of 5 cm. This cartridge (1) is provided with a central reservoir (11) and will be described in more detail with reference to FIGS. 3 and 4. In the present embodiment, the capacity of the reservoir is 400 μl. Its floor is flat but it should be noted that in other embodiments, it may be domed to facilitate the passage of fluid into the chambers without the formation of air bubbles, in particular at the end of distribution when the reservoir is almost empty.

The system also comprises a heating plate (2) in direct contact with the lower surface of cartridge (1) and means (3) for displacing cartridge (1) with respect to the heating plate (2). These displacement means include a micrometer (31) connected to two axles (32) that co-operate with two lugs (183) on cartridge (1) to cause it to move in a rotary motion on the heating plate (2), the latter remaining stationary.

The system described also comprises a piston (41) for co-operating with said reservoir (11) and a fixed optical fluorescence excitation/measuring device (5) (emitting source to excite at a given programmable wavelength and a receiver for the emitted fluorescence) located above the cartridge (1) and the heating plate (2).

As can be seen in FIG. 2A, the heating plate (2) is constituted by three metallic blocks (21, 22, 23) (hereinafter termed thermoblocks) in the form of sections of disks. It should be noted here that in this embodiment, these thermoblocks are substantially the same size, but in other embodiments they may be of a different size, "size" meaning its angular extent viewed from above. Each thermoblock (21, 22, 23) is designed to be able to be brought to a constant, programmable temperature corresponding to one of the phases (denaturation, primer annealing or elongation) of the amplification cycles (PCR), i.e., in general, respectively 94° C. for denaturation, 72° C. for elongation and between 30–40° C. and 65–70° C. for primer annealing depending on the Tm (hybridisation temperature) of the primers used. The temperatures of the thermoblocks can be controlled using any means known in the art.

Referring to FIG. 3, cartridge (1) is provided with a central reservoir (11) with a capacity of 400 μl connected to 36 reaction chambers (13) by the same number of channels (12) uniformly distributed over the entire periphery of the cartridge (FIG. 3 only shows a few of the channels and chambers). These reaction chambers (13) are provided with vents (14) opening at the edge of the cartridge (1). In the present embodiment, the channel diameter is 0.2 mm and the volume of the reaction chambers is 2.5 microliters. In other embodiments, this diameter and volume may, of course, be different.

As already described, the cartridge (1) is also provided with two lugs (183) each pierced by an orifice to allow the passage of an axle (32) connected to the micromotor (31).

Figure 4:
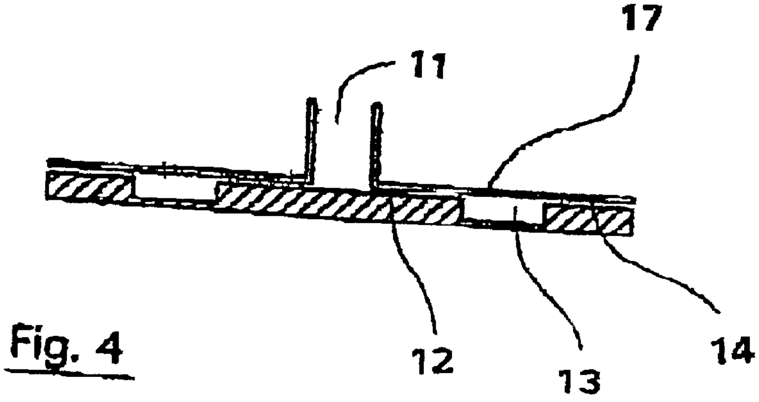
FIG. 4 shows a cross section of the cartridge along the line AA.

In FIG. 4, the reaction chambers have a depth of 1 mm. Their floor is about 0.2 mm thick. This is sufficiently thin to facilitate good thermal exchange between the chambers (13) and the thermoblocks (21, 22 and 23). The upper portions of reach chambers (13) are closed by a transparent wall (17), also forming the wall of reservoir (11).

The illustrated device is used as follows:

Central reservoir (11) is intended to receive the nucleic acid sample to be analysed as well as all the components required for the amplification reaction, and optionally a fluorescent nucleic acid reporter (this ensemble is termed the fluid), with the exception of primers pre-deposited in each peripheral reaction chamber (10).

In the present embodiment, the operator places 90 μl (i.e., 36 times 2.5 μl) of fluid, including 75 ng of nucleic acids, in the central reservoir. The concentrations of the reagents in said fluid are as follows:

dNTPs: 200 μM

Teq buffer: 1×

$MgCl_2$: 1.5 mM

Taq: 4 U

SybrGreen (registered trade mark): 1×

$H_2O$: qsp

Each chamber (10), apart from the few with negative controls, contains two specific primers for a target sequence to be amplified, and optionally one or more labelled probes, allowing specific subsequent fluorescence measurement. In the present embodiment, 10 ng of each primer has been deposited in each chamber apart from those acting as the negative control.

After partially filling reservoir (11) with the fluid, wherein the volume is equal to the sum of the volumes of the chambers (the volume of one chamber is defined as being the product of the surface area of the "floor" multiplied by its depth), piston (41) is actuated to distribute the fluid in the plurality of reaction chambers (13). This piston can increase the pressure in reservoir (11) and allows the passage of fluid into the channels towards the chambers. The rate of displacement of the piston in the reservoir is about 1 mm per second and said displacement is halted at a level that depends on the volume of fluid to be distributed to the chambers.

The small diameter of channels (12) prevents fluid diffusion from reservoir (11) to channels (12) and chambers (13) under gravity (on this scale, processes that can usually be ignored, such as capillary forces, become important, and in this case are sufficient to retain the fluid in the reservoir). Because of vents (14), the air present in the chambers (13) is evacuated, which ensures that they are filled.

Thermoblocks (21, 22, 23) are heated to the three temperatures corresponding to the three temperatures of the PCR phases (or to slightly higher temperatures to compensate for any heat losses between the heating plate (2) and cartridge (1)) and the displacement means (3) are actuated to move the cartridge (1) to cause each reaction chamber to pass successively, and for the desired number of times, over the three thermoblocks.

More precisely, block (21) is heated to the temperature corresponding to the denaturation phase (94° C.), thermoblock (22) is heated to the temperature corresponding to the annealing phase (36° C.) and thermoblock (23) is heated to the temperature corresponding to the elongation phase (72° C.).

In the present embodiment, micromotor (31) for displacement means (3) is designed to cause rotation of cartridge (1) by 10 degrees every 2.5 seconds (i.e., one PCR cycle in 1.5 minutes). However, in other embodiments, this movement may be at a different rate and may be continuous instead of being intermittent.

It should be noted that the optical device (5) is provided above the corresponding block 23 heated to a temperature corresponding to the elongation temperature, and more particularly in a location that corresponds to the end of the elongation phase. Clearly, the optical device (5) can be positioned in a different location, selected primarily as a function of the chemicals used for the amplification detection. As an example, using TaqMan chemicals or non specific fluorescence, it is logical to make the measurement at the end of the extension phase, as described above. In contrast, the use of a Molecular Beacons™ type chemicals means that the measurement should be made at the annealing stage.

The system enables a large number of reaction chambers to be filled rapidly and in a reproducible manner and allows the contents of the chambers to undergo PCR; it also allows fluorescence measurements to be made for each PCR cycle.

The embodiment described above is not intended to limit the scope of the invention. Thus, a number of modifications can be made thereto without departing from the scope of the invention.

Example 2

Improved Circular Cartridge

FIGS. 5 to 10 show an example of a circular cartridge with certain modifications over the cartridge of Example 1.

Figure 6:
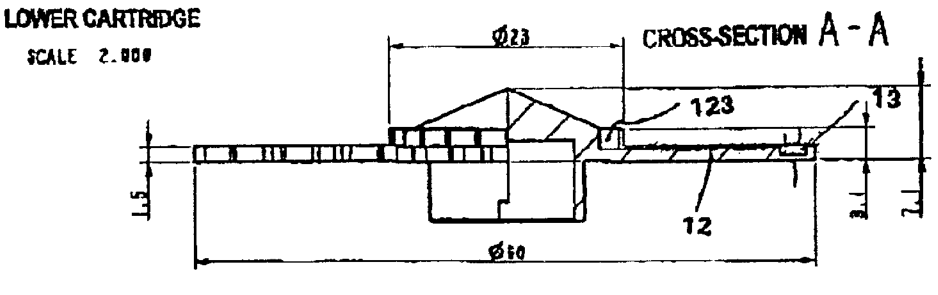
FIG. 6 shows a cross section of the lower cartridge along line AA in FIG. 5.
Figure 5:
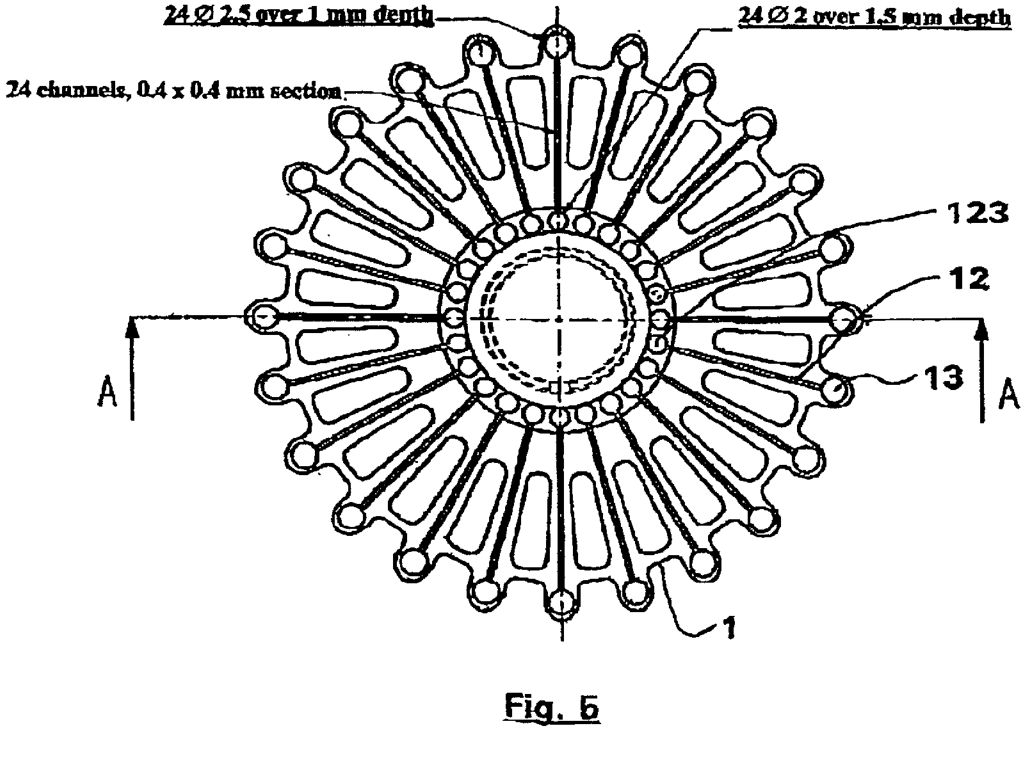
FIG. 5 shows a top view of the lower portion (base) of a second particular embodiment of the cartridge of the present invention. The dimensions are given by way of indication only and are in no way limiting.
Figure 8:
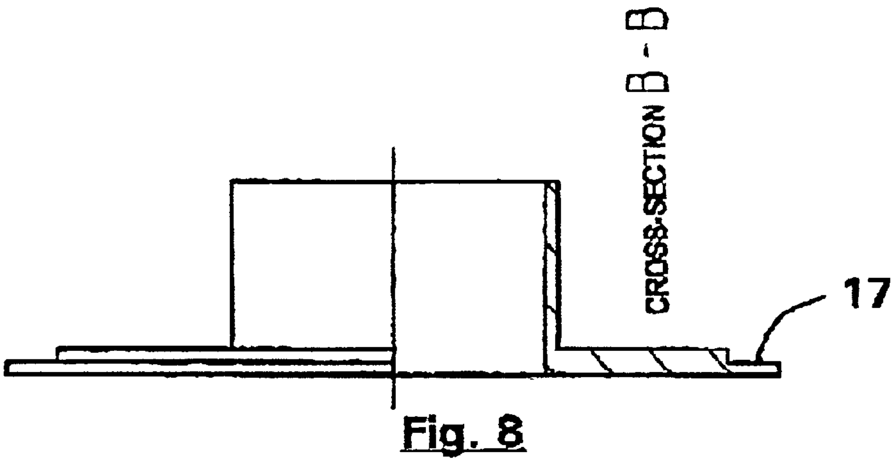
FIG. 8 shows a cross section of this upper cartridge, along line BB in FIG. 7.
Figure 7:
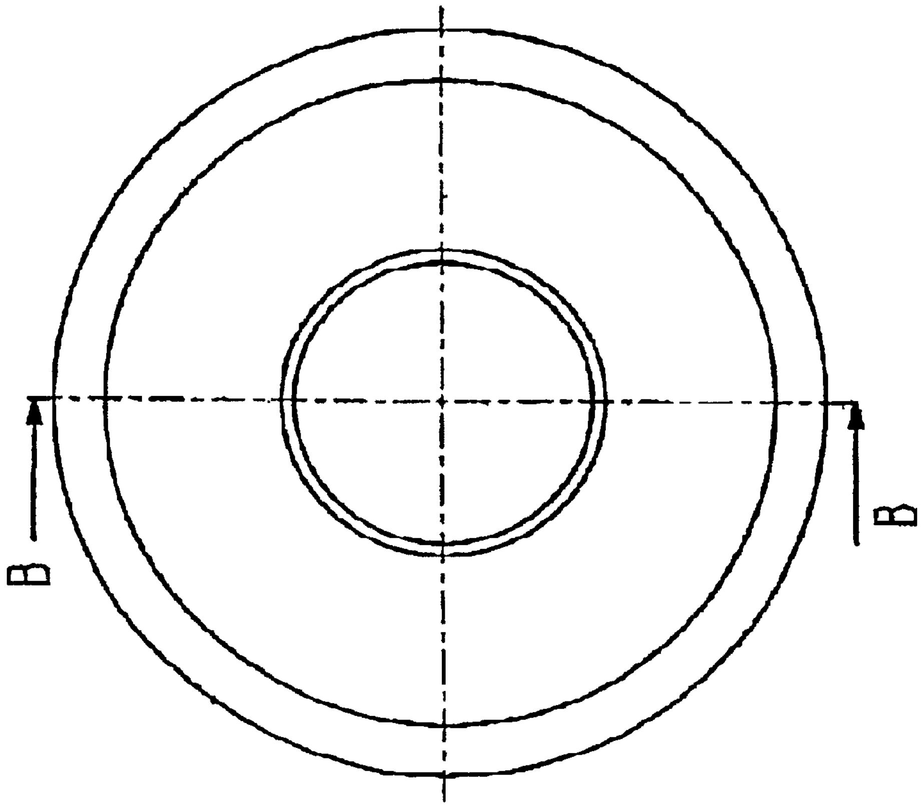
FIG. 7 shows a top view of the upper portion (cover) of the cartridge shown in FIGS. 5 and 6.
Figure 9:
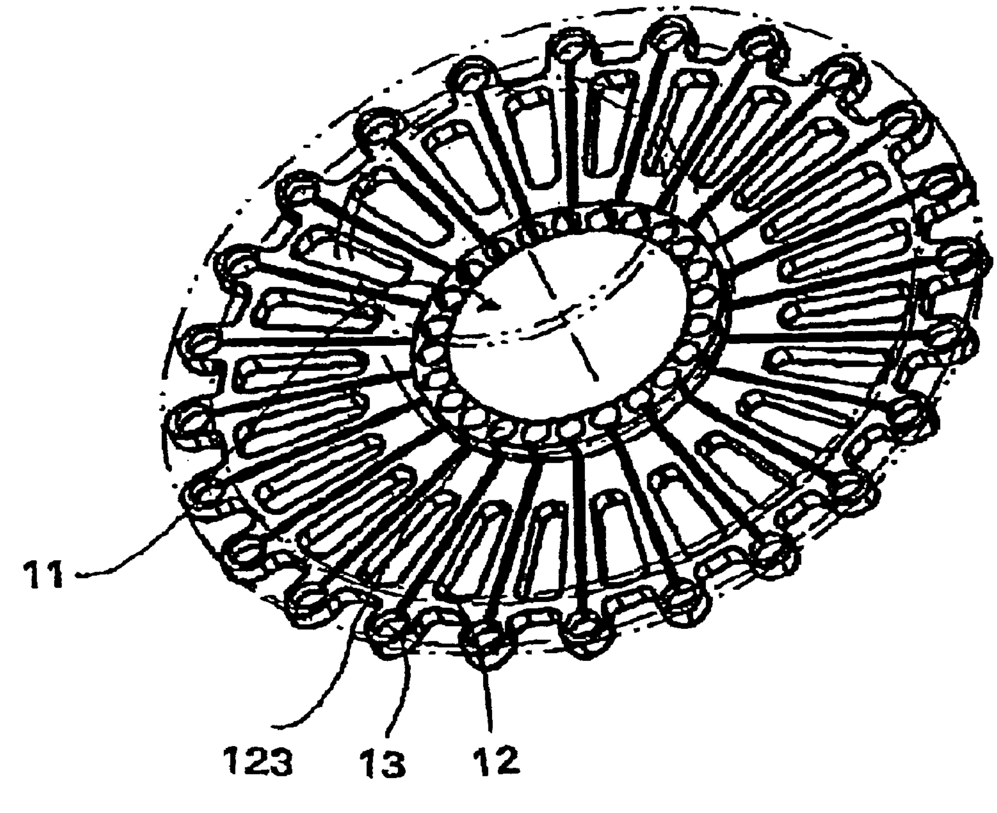
FIG. 9 shows a complete cartridge, constituted by a base shown in FIGS. 5 and 6 (solid lines) and the cover shown in FIGS. 7 and 8 (dotted lines)

This cartridge is provided for use in a closed system, i.e., the reaction chambers (13) have no other opening apart from the inlet for channel (12). The cartridge is constituted by two elements that fit one in the other, the lower portion, or base, is shown in FIGS. 5 and 6, and the upper portion, or cover, is shown in FIGS. 7 and 8. The assembly of the two portions is shown in FIGS. 9 and 10.

This cartridge is charged as follows:

The operator places the extract of nucleic acids to be analysed in the central reservoir. The disposable cartridge is placed in the instrument. This latter produces an underpressure in the cartridge (P=0.05 bars, approximately), for example using a pump (42). The pressure is then re-established, which enables the fluids to engage in the channels and to fill the peripheral reaction chambers. Thus, compared with the instrument of Example 1, the fluid is no longer distributed by an increase in pressure but by an underpressure, which has the advantage of not requiring a vent and thus allowing the system to be operated as a closed system.

If necessary, a plurality of sub-reservoirs rather than a single reservoir can be provided, which has the advantage of simultaneously treating several samples.

The bottom of the reservoir is conical to allow a fluid to be distributed to its periphery, i.e., close to the inlets to the channels.

An anti-reflux system is provided at the junction between the channels and the reservoir, constituted by a vertical channel portion (128), which firstly prevents cross-contamination in the event of accidental return of fluid towards the central portion or in the case where all of the fluid is not engaged in the channel, and also, once distribution is complete but before the PCR, can block the channels by means of a cap the indentations of which match these vertical inlets, to allow operation as a closed system (no contamination, no evaporation).

The cartridge is plastic, preferably polycarbonate, as that polymer has advantageous physical and optical properties and advantageous thermal properties.

The channel dimensions are, for example, 0.4×0.2 mm (half-moon) in cross section.

The disposable cartridge is, for example, 100 mm in diameter, with 80 chambers and 1 to 8 sub-chambers.

As shown in FIG. 10, the bottom of cartridge (1) has a central projecting portion (181) comprising a notch (182), such that the projecting portion (181) nests into the heating plate (2) and connects the cartridge (1) with displacement means (3) at a driver or axle (32) caused to move by a micromotor (31). The projecting portion (181) allows the cartridge to be positioned with respect to a plate (2) such as that shown in FIG. 2B, and can ensure its connection with the moving means (3).

The reaction chambers are charged with specific primers for the target sequences and, if necessary, with probes of the TaqMan™ type or others that are specific for said targets. Depending on the application, the targets will be viral or bacterial genes, the junctions between a transgene and the genome of a plant to detect and/or identify certain genetic modifications, etc.

A variation of the cartridge described above, comprising 36 reaction chambers with a volume of 8 μl and channels with a 0.3 mm diameter, was used to carry out a test for detecting Salmonella bacteria. 288 μl (i.e., 36 times 8 μl) of the following solution was placed in the central reservoir:

DUTP: 400 μM
dNTPs: 200 μM
Taq buffer: 1×
$MgCl_2$: 3 mM
Taq: 15 U
TWEEN (registered trade mark): 0.007%
SybrGreen (registered trade mark): 0.1×
Genomic DNA from Salmonella enteritidis: 1 ng
$H_2O$: qsp 1.6 picomoles of FinA1 and FinA2 primers described by Cohen, Mechanda et al., 1990, was deposited in the reaction chambers.

This experiment produced positive results, as expected.

Example 3

Rectangular Cartridge

In this example, illustrated in FIG. 11, the reservoir is no longer central but to one side and the motion of the cartridge is no longer necessarily rotational, but may be translational.

The distribution and closing modes can be exactly as described for the circular mode described for Example 2.

Figure 12:
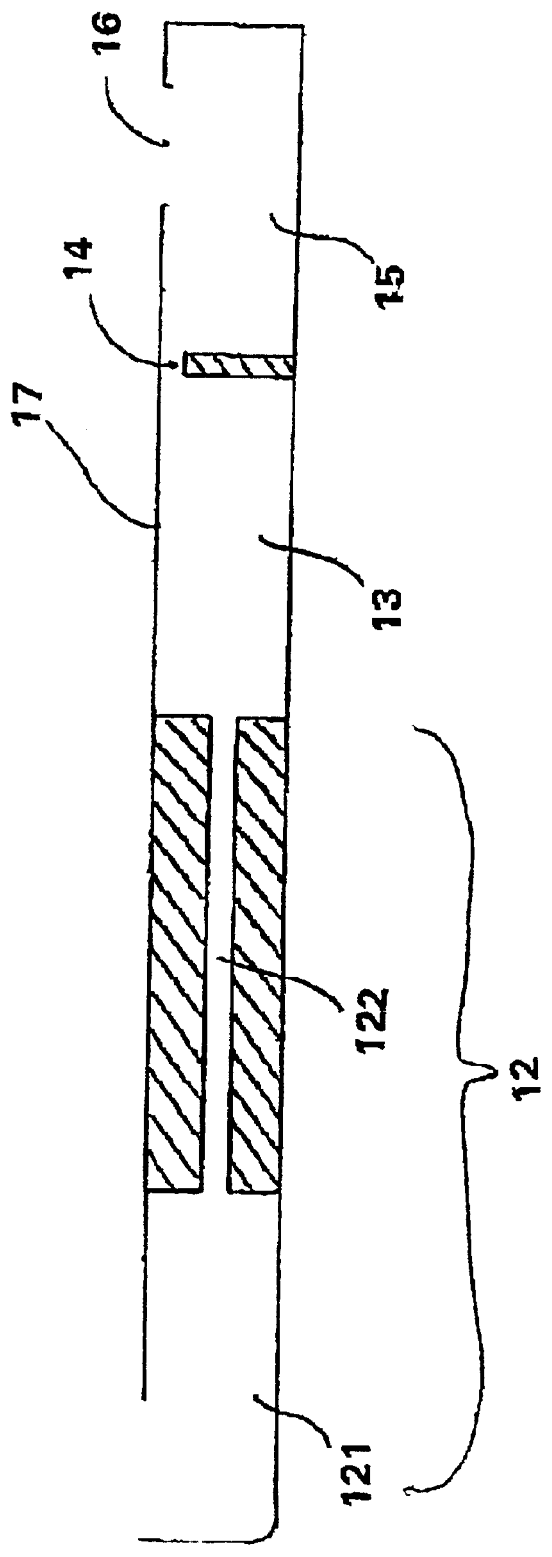
FIG. 12 shows a schematic view of a channel (12) with a pressure drop device.

Alternatively, the fluids can be distributed by increasing the pressure. They enter into the first portion of the channel (121) wherein the sum of the volumes is slightly lower than the volume of sample to be analysed (nucleic acid extract). The second portion of channel (122) is constituted by a glass capillary with a much smaller diameter, incorporated into the plastic system, as shown in FIG. 12. Its advantage is to create a pressure drop phenomenon, allowing the first portion of the channels to be homogeneously filled (if one channel fills faster than another as the pressure increases, this phenomenon stops fluid advancing in the filled channels until the others have been filled). This allows the volumes for each channel to be "pre-calibrated" and ensures that the different downstream chambers (13) are homogeneously filled. At the end of the chambers are vents that open into cells (15) which have holes in the top to allow any surplus fluid that would leave via said vents to be recovered and to allow said cells (15) to be closed using adhesive tape to prevent evaporation. The volume (and shape) of the chambers is equal to that of the first portion of the channels.

The channel is 0.4 mm in diameter, i.e., one channel per mm if the space between the channels is 0.6 mm. Thus, a cartridge that is 8 cm long contains 80 chambers.

Two possibilities can be envisaged to close the channel at the reservoir.

The first possibility consists of using an indented cap as in Example 2. The piston that increases the pressure and said cap are then one and the same. In this case, the piston must be released between the step for distributing the fluids by pressure and this closing step, so that closing does not cause a fresh increase in pressure which would bring the fluid beyond the chambers.

The second possibility consists of depositing (excess) oil above the fluids. Once the chambers are filled, channels (121) are at least partially filled with oil, preventing contamination and evaporation.

REFERENCES

Cohen, H. J., S. M. Merchanda, et al., (1996). "PCR amplification of the fimA gene sequence of Salmonella typhimurium, a specific method for detection of Salmonella spp" *Appl. Environ Microbiol* 62 (12): 4303–8.

Gibson, U. E., C. A. Heid et al., (1996). "A novel method for real-time quantitative RT-PCR". *Genome Res.* 6 (10): 995–1001.

Heid, C. A., J. Stevens et al., (1996). "Real-time quantitative PCR". *Genome Res* 6 (10): 986–94.

Williams, P. M., T. Giles et al., (1998). "Development and application of real-time quantitative PCR". *In F: Ferré (Ed.). Gene Quantification. Birkhaüser, Boston.*

What is claimed is:

1. A device for carrying out enzymatic and/or molecules biological reactions requiring at least two different incubation temperatures, characterized in that it comprises:

at least one cartridge having a plurality of reaction chambers and a reservoir, said reaction chambers being connected to the reservoir via channels, at least one heating plate having at least two distinct zones that can be heated to at least two different temperatures;

means for relative displacement between said cartridge and said plate, allowing a cyclic variation of the temperature of the reaction chambers.

2. The device of claim 1, in which the enzymatic reaction is a thermodependent chain amplification of nucleic acid sequences and in which the zones of the heating plate can be heated to at least two different temperatures, corresponding to phases in the nucleic acid amplification cycles.

3. The device of claim 2, wherein:

primers specific for the target sequences to be amplified are predistributed in the reaction chambers;

the reservoir is intended to receive a fluid composed of a sample of nucleic acids to be analysed and the reagents required for a polymerase chain amplification reaction with the exception of primers;

the heating plate has three distinct zones that can be heated to three different temperatures corresponding to the three phases of polymerase chain reaction amplification cycles.

4. The device of claim 2, for real-time thermodependent chain amplification of nucleic acid sequences, which comprises optical means for fluorescence excitation/measurement, disposed so as to excite and measure the fluorescence of the contents of the reaction chambers in each cycle.

5. The device of claim 2, in which the cartridge comprises a plurality of reaction chambers and at least one reservoir and having the following characteristics:

each reaction chamber is connected to the reservoir via a channel having a cross section included in a circle with a diameter of less than 3 mm;

the capacity of the reservoir is less than 10 ml;

the disposition of the reaction chambers and the channels with respect to the reservoir allows a fluid to be homogeneously distributed into the reaction chambers from the reservoir.

6. The device of claim 2, in which the distinct zones for heating the plate are distributed into at least two or three disk portions.

7. The device of claim 2, in which said heating plate is fixed and said cartridge is moved by means of displacement means.

8. The device of claim 2, in which said cartridge is fixed and said heating plate is moved by means of displacement means.

9. The device of claim 2, in which said displacement means cause rotation of said cartridge and/or said heating plate.

10. The device of claim 2, in which the cartridge is in direct contact with the heating plate.

11. The device of claim 2, in which the plate is provided with a coating encouraging relative displacement between said cartridge and said plate.

12. The device of claim 2, in which the heating plate comprises two or three distinct thermoblocks connected to means for programming their temperatures.

13. The device of claim 2, in which the bottom of the cartridge has a central projecting portion comprising a notch, and the displacement means include at least one driver co-operating with said notch to cause said cartridge to move in a rotary motion.

14. The device of claim 2, comprising optical means for fluorescence excitation/measurement disposed above or to the side of the cartridge.

15. The device of claim 2, further comprising means for supplying fluid present in the reservoir to the reaction chambers.

16. The device of claim 15, in which said supply means include a piston device, and the fluid is supplied to the reaction chambers by increasing the pressure.

17. The device of claim 15, in which said supply means include a pump and the fluid is supplied to the reaction chambers by reestablishing the pressure after establishing an underpressure.

18. The device of claim 17, in which the reaction chambers of the cartridge are closed.

* * * * *